(12) United States Patent
Arai et al.

(10) Patent No.: US 11,559,273 B2
(45) Date of Patent: Jan. 24, 2023

(54) MAMMOGRAPHY APPARATUS AND PROGRAM

(71) Applicant: FUJIFILM Corporation, Tokyo (JP)

(72) Inventors: Takahisa Arai, Kanagawa (JP);
Takeyasu Kobayashi, Kanagawa (JP);
Shunsuke Kodaira, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 16/794,154

(22) Filed: Feb. 18, 2020

(65) Prior Publication Data

US 2020/0261046 A1 Aug. 20, 2020

(30) Foreign Application Priority Data

Feb. 20, 2019 (JP) .............. JP2019-027982

(51) Int. Cl.
*G06K 9/00* (2022.01)
*A61B 6/00* (2006.01)
*G06T 7/00* (2017.01)
*A61B 8/08* (2006.01)

(52) U.S. Cl.
CPC ............ *A61B 6/5217* (2013.01); *A61B 6/488* (2013.01); *A61B 6/502* (2013.01); *G06T 7/0014* (2013.01); *A61B 8/0825* (2013.01); *A61B 8/5223* (2013.01); *G06T 2200/24* (2013.01); *G06T 2207/10012* (2013.01); *G06T 2207/10116* (2013.01); *G06T 2207/30068* (2013.01); *G06T 2207/30096* (2013.01); *G06T 2207/30204* (2013.01)

(58) Field of Classification Search
CPC ....... A61B 6/5217; A61B 6/488; A61B 6/502; A61B 8/0825; A61B 8/5223; G06T 7/0014; G06T 2200/24; G06T 2207/10012; G06T 2207/10116; G06T 2207/30068; G06T 2207/30096; G06T 2207/30204
See application file for complete search history.

(56) References Cited

U.S. PATENT DOCUMENTS

2002/0172414 A1 11/2002 Muller et al.
2012/0155734 A1 6/2012 Barratt et al.
(Continued)

FOREIGN PATENT DOCUMENTS

DE 102011080682 2/2013
JP 2005510326 4/2005
(Continued)

OTHER PUBLICATIONS

"Search Report of Europe Counterpart Application", dated Jul. 8, 2020, p. 1-p. 9.
(Continued)

*Primary Examiner* — Atiba O Fitzpatrick
(74) *Attorney, Agent, or Firm* — JCIPRNET

(57) ABSTRACT

A mammography apparatus includes a diagnostic image acquisition unit that acquires a diagnostic image in which a calcification as a biopsy target is marked; a scout image acquisition unit that acquires a scout image obtained by imaging a mamma undergoing the biopsy from a specific direction; and a display unit that highlights a calcification (candidate for biological tissue examination) in the scout image which matches at least the marked calcification in the diagnostic image.

24 Claims, 9 Drawing Sheets

(56) References Cited

U.S. PATENT DOCUMENTS

| | | | |
|---|---|---|---|
| 2015/0199790 A1* | 7/2015 | Kopylov | A61B 6/502 345/660 |
| 2016/0235380 A1* | 8/2016 | Smith | A61B 6/482 |
| 2017/0337336 A1* | 11/2017 | Weidner | A61B 6/502 |
| 2018/0033143 A1* | 2/2018 | Buelow | A61B 6/5217 |
| 2018/0078231 A1 | 3/2018 | Butani et al. | |
| 2018/0235559 A1* | 8/2018 | Mc Carthy | A61B 6/4476 |
| 2019/0051023 A1* | 2/2019 | Bernard | A61B 6/502 |
| 2019/0066260 A1* | 2/2019 | Suehling | A61B 6/5247 |

FOREIGN PATENT DOCUMENTS

| | | |
|---|---|---|
| JP | 2013501290 | 1/2013 |
| JP | 2016533803 | 11/2016 |
| WO | 03046810 | 6/2003 |

OTHER PUBLICATIONS

"Office Action of Japan Counterpart Application" with English translation thereof, dated Dec. 21, 2021, p. 1-p. 10.

\* cited by examiner

MAMMOGRAPHY APPARATUS AND PROGRAM

CROSS-REFERENCE TO RELATED APPLICATIONS

This application claims priority under 35 U.S.C § 119(a) to Japanese Patent Application No. 2019-027982 filed on 20 Feb. 2019. The above application is hereby expressly incorporated by reference, in its entirety, into the present application.

BACKGROUND OF THE INVENTION

1. Field of the Invention

The present invention relates to a mammography apparatus for imaging a mamma of a test subject using radiation such as X-rays, and a program for driving the mammography apparatus.

2. Description of the Related Art

In the related art, the mammography apparatus is used for breast cancer screening, a biological tissue examination (hereinafter, referred to as a biopsy), and the like. Since the breast cancer is closely associated with a calcification, in the breast cancer screening, it is common to search for a calcification using an image captured by using the mammography apparatus (hereinafter, referred to as a mammography image) and to diagnose whether the found a calcification is associated with the breast cancer. Then, in a case where a calcification that may be associated with the breast cancer is found, a biopsy is performed. The biopsy is for a definitive diagnosis.

Meanwhile, a method of positioning two images for medical use is known (JP2013-501290A, corresponding to US2012/155734A1). In addition, an image analysis method having functions of displaying a 3D rendering model and performing centering around the coordinates relating to the diagnostic findings is known (JP2005-510326A, corresponding to WO2013/046810A1).

SUMMARY OF THE INVENTION

In a case where a biopsy is performed, a biopsy target specified using an image used for diagnosis (hereinafter, referred to as a diagnostic image) has to be searched for again using an image captured in case of performing a biopsy (hereinafter, referred to as a biopsy image), but there was no auxiliary means to find the target, which is specified using the diagnostic image, in the biopsy image. Therefore, during the biopsy, an incorrect target (target different from the target specified using the diagnostic image) may be collected, which becomes a burden on a test subject.

An object of the invention is to specify a candidate for a target in a biopsy image using a diagnostic image in a case where a biopsy is performed.

A mammography apparatus according to an aspect of the invention comprises a diagnostic image acquisition unit that acquires a diagnostic image which is a mammography image used for diagnosis and in which a target of a biological tissue examination is marked; a scout image acquisition unit that acquires a scout image obtained by imaging a mamma undergoing the biological tissue examination from a specific direction; and a display unit that highlights a candidate for the biological tissue examination in the scout image which matches at least the marked target in the diagnostic image.

It is preferable that a tissue similarity degree calculation unit recognizes the "candidate" in the scout image and calculates a tissue similarity degree which is a similarity degree between the "candidate" in the scout image and the marked target in the diagnostic image, and a determination unit determines whether the candidate matches the target using the tissue similarity degree.

It is preferable that the display unit displays a value of the tissue similarity degree.

It is preferable that the display unit highlights the "candidate" of which the tissue similarity degree is equal to or greater than a first threshold.

It is preferable that the mammography apparatus includes an image similarity degree calculation unit that calculates an image similarity degree which is a similarity degree for a partial image or a whole image between the diagnostic image and the scout image, and the display unit determines whether to highlight the "candidate" using the image similarity degree.

It is preferable that the display unit highlights the "candidate" in a case where the image similarity degree is equal to or greater than a second threshold.

It is preferable that the mammography apparatus includes a warning notification unit that notifies of a warning at least in a case where there is no candidate to be highlighted by the display unit.

It is preferable that the warning notification unit prompts recapturing of the scout image.

It is preferable that the display unit displays a position of the "candidate" in the scout image which matches the marked target in the diagnostic image, by highlighting.

It is preferable that the mammography apparatus includes a stereo image acquisition unit that acquires a stereo image obtained by imaging the mamma undergoing the biological tissue examination from an inclination direction which is inclined with respect to the specific direction from which the scout image is captured; and a stereo image recognition unit that recognizes the "candidate" in the stereo image, and associates the "candidate" in the stereo image with the marked target in the diagnostic image or the "candidate" in the scout image which matches the marked target in the diagnostic image, and the display unit highlights the candidate matching the marked target in the diagnostic image among the candidates in the stereo image.

It is preferable that the stereo image recognition unit calculates a second tissue similarity degree which is a similarity degree between the "candidate" in the stereo image and the marked target in the diagnostic image or the "candidate" in the scout image which matches the marked target in the diagnostic image, and the display unit highlights at least the "candidate" having the highest second tissue similarity degree among the "candidates" in the stereo image.

It is preferable that the stereo image acquisition unit prohibits capturing of the stereo image in a case where there is no "candidate" in the scout image, which matches the marked target in the diagnostic image.

It is preferable that the mammography apparatus includes a tomosynthesis image acquisition unit that acquires a series of tomosynthesis images of the mamma undergoing the biological tissue examination; and a tomosynthesis image recognition unit that recognizes the target of the biological tissue examination in the series of tomosynthesis images, and associates the candidate in each tomosynthesis image with the marked target in the diagnostic image or the candidate in the scout image which matches the marked target in the diagnostic image, and the display unit selects and displays some of the tomosynthesis images from among the series of tomosynthesis images using a recognition result of the tomosynthesis image recognition unit.

It is preferable that the tomosynthesis image recognition unit calculates a third tissue similarity degree which is a similarity degree between the "candidate" in the tomosynthesis image and the marked target in the diagnostic image or the "candidate" in the scout image which matches the marked target in the diagnostic image, and the display unit displays the tomosynthesis image including at least a calcification having the highest third tissue similarity degree among the "candidates" in the series of tomosynthesis images.

It is preferable that the tomosynthesis image acquisition unit prohibits imaging for obtaining the tomosynthesis image in a case where there is no "candidate" in the scout image, which matches the marked target in the diagnostic image.

It is preferable that the mammography apparatus includes a warning notification unit that notifies of a warning to prompt marking of the calcification in a case where there is no marked target in the diagnostic image.

It is preferable that the mammography apparatus includes a marking unit that recognizes the "candidates" in the diagnostic image and marks some or all of the recognized "candidates" in a case where there is no marked target in the diagnostic image.

It is preferable that the scout image acquisition unit acquires the scout image of which at least one or a plurality conditions among use or non-use of a grid, a tube voltage of a radiation tube, and a dose of radiation are the same as the diagnostic image.

It is preferable that the scout image acquisition unit acquires the scout image in which a grid having the same grid ratio as a grid used for capturing the diagnostic image is used in a case where the scout image in which the grid is used is acquired.

It is preferable that the scout image acquisition unit acquires the scout image subjected to the same image processing as the diagnostic image.

It is preferable that the tissue similarity degree calculation unit recognizes the "candidate" in the scout image by pattern matching and calculates the tissue similarity degree.

It is preferable that the tissue similarity degree calculation unit outputs a probability that the candidate for the biological tissue examination in the scout image is the marked target in the diagnostic image, as the tissue similarity degree by using a learned model that outputs the probability by inputting the diagnostic image in which the target of the biological tissue examination is marked and the scout image.

A program according to an aspect of the invention is a program driving a mammography apparatus including a display unit that highlights a candidate for a biological tissue examination in a biopsy image captured in the biological tissue examination, and the program causes an arithmetic operation device of the mammography apparatus or an arithmetic operation device cooperating with the mammography apparatus to calculate the tissue similarity degree used for determining the "candidate" to be highlighted by the display unit, by using a learned model that outputs a position of the "candidate" in the biopsy image and a tissue similarity degree which is a similarity degree between the "candidate" in the biopsy image and a marked target in the diagnostic image by inputting the biopsy image and the diagnostic image in which the target of the biological tissue examination is marked.

According to the invention, it is possible to specify a candidate for a target in a biopsy image using a diagnostic image in a case where a biopsy is performed.

DESCRIPTION OF THE PREFERRED EMBODIMENTS

First Embodiment

Figure 1:
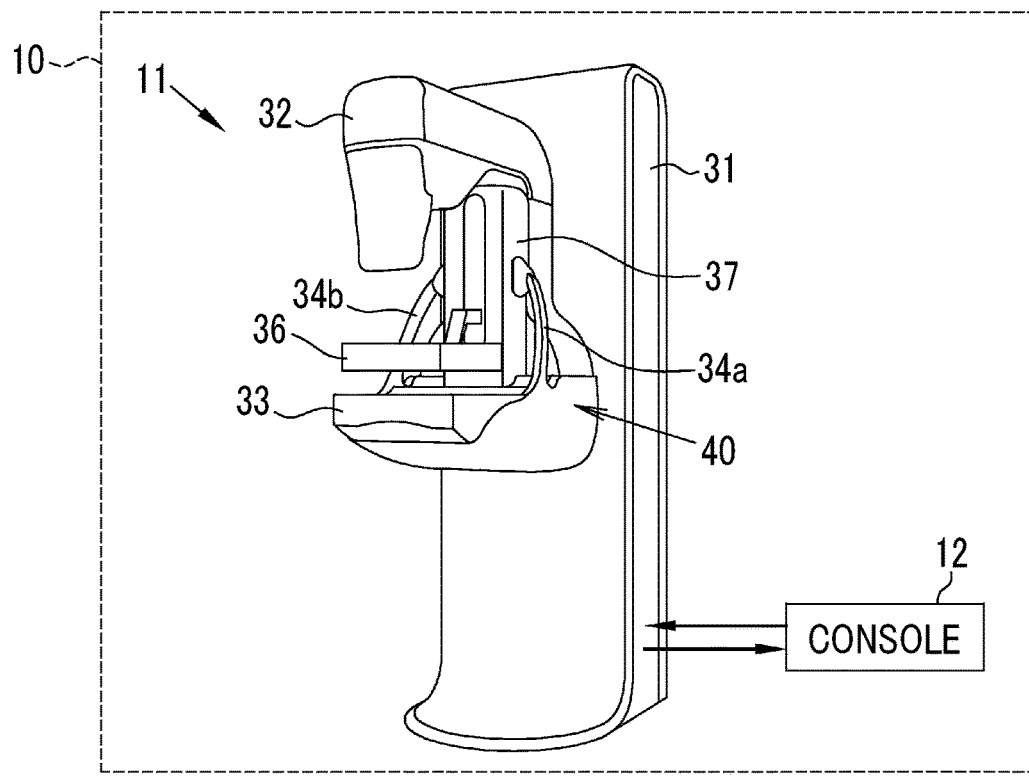
FIG. 1 is an explanatory diagram showing a configuration of a mammography apparatus.

As shown in FIG. 1, a mammography apparatus 10 includes an apparatus body 11 which images a mamma of a test subject using X-rays, and a console 12 which controls the apparatus body 11.

The apparatus body 11 includes a prop 31, an X-ray generation part 32, an imaging stand 33 with a built-in X-ray imaging part, a pressing plate 36, a lifting/lowering part 37, and the like. In addition, the X-ray generation part 32 and the imaging stand 33 are integrated and configure a movable part 40 which adjusts a position according to a test subject in the apparatus body 11.

The imaging stand 33 is a stage on which a mamma of a test subject is placed, and clamps the mamma of the test subject using the pressing plate 36 during imaging. The X-ray imaging part (not shown) built in the imaging stand 33 includes a flat panel detector (FPD) or the like which images a subject using, for example, radiation, and a grid for removing scattered rays (stationary Lysholm blende or mobile bucky blende). The mammography apparatus 10 has multiple types of grids which are replaceable according to the imaging conditions, and can perform imaging in which the grid is not used. In addition, a grip part 34a that the test subject grips with the right hand and a grip part 34b that the test subject grips with the left hand are attached to the imaging stand 33. The grip part 34a and the grip part 34b are a so-called arm rest.

The pressing plate 36 presses the mamma of the test subject, which is placed on the imaging stand 33, and makes the mamma flat. This is to reduce the overlap of normal mammary glands and make it easier to find a candidate for a lesion such as a calcification. The lifting/lowering part 37 lifts or lowers the pressing plate 36 with respect to the imaging stand 33. In this manner, the lifting/lowering part 37 supports the pressing plate 36 approximately parallel to the imaging stand 33 and at a specific distance according to the thickness of the mamma.

The movable part 40 is rotatable within a predetermined angle range while maintaining the relative position and direction of the X-ray generation part 32 and the imaging stand 33. Therefore, the apparatus body 11 can perform imaging with the imaging stand 33 being disposed horizontally or the imaging stand 33 being disposed obliquely with respect to the horizontal. Specifically, the apparatus body 11 can perform craniocaudal imaging (CC imaging) in which a mamma is imaged from a craniocaudal direction, with the imaging stand 33 being disposed horizontally. In addition, the apparatus body 11 can perform mediolateral oblique imaging (MLO imaging) in which a mamma is imaged from a mediolateral oblique direction, with the imaging stand 33 being disposed obliquely.

Further, the X-ray generation part 32 of the movable part 40 is rotatable within a predetermined range while the positions of the imaging stand 33 and the pressing plate 36 are fixed. In this manner, the apparatus body 11 can perform so-called stereo imaging and tomosynthesis imaging. The stereo imaging is an imaging aspect in which the mamma of the test subject fixed at specific position and direction (for example, position and direction of the CC imaging) is imaged from one or a plurality of inclination directions with different inclination angles and a fluoroscopic image from the inclination direction (hereinafter, referred to as a stereo image) is obtained. In addition, the tomosynthesis imaging is an imaging aspect in which a tomographic image (hereinafter, referred to as a tomosynthesis image) of a mamma of a test subject is obtained using images of the mamma of the test subject fixed at the specific position and direction, which are captured from a plurality of inclination directions.

Figure 2:
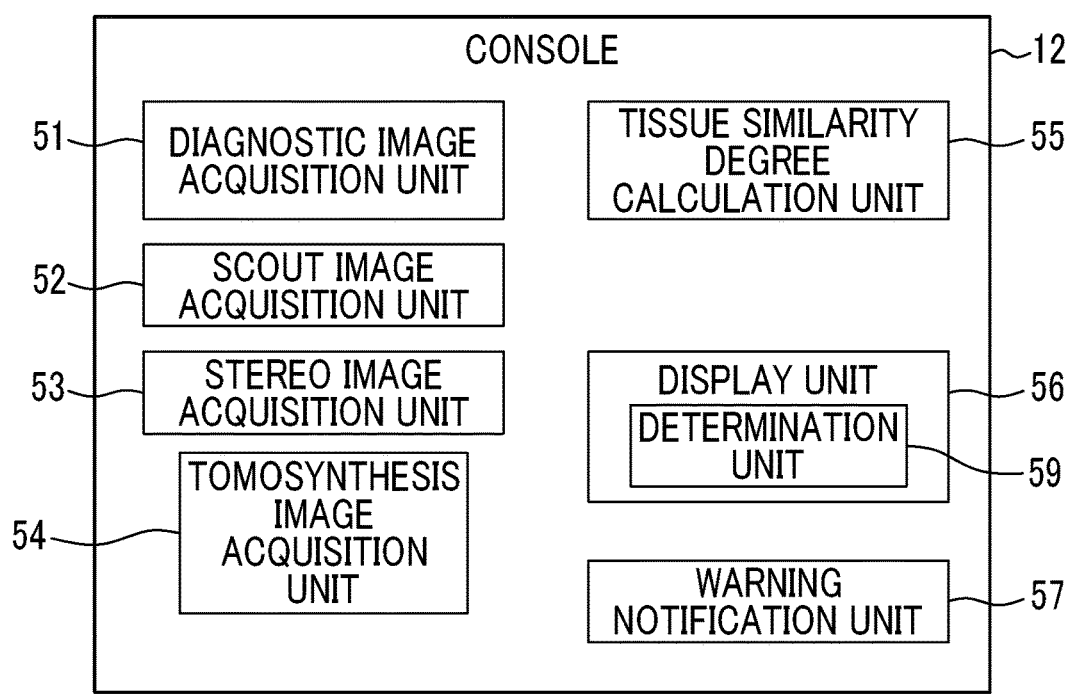
FIG. 2 is a block diagram showing a configuration of a console.

As shown in FIG. 2, the console 12 includes a diagnostic image acquisition unit 51, a scout image acquisition unit 52, a stereo image acquisition unit 53, a tomosynthesis image acquisition unit 54, a tissue similarity degree calculation unit 55, a display unit 56, and a warning notification unit 57.

The diagnostic image acquisition unit 51 acquires diagnostic images from a radiology information system (RIS), a picture archiving and communication system (PACS), a hospital information system (HIS), or the like which is directly or indirectly connected to the mammography apparatus 10. The diagnostic image is a mammography image used for diagnosis, and a mammography image in which a target of the biological tissue examination is marked is obtained. The target of the biological tissue examination is simply a biopsy target, for example, a calcification. Hereinafter, in this specification, it is assumed that the target of the biological tissue examination is a "calcification" and the target of the biological tissue examination is simply referred to as a calcification. Note that, for a lesion or a portion that could be a lesion, regardless of a specific form of the tissue or structure thereof, a tissue or the like other than calcifications can be a target of the biological tissue examination.

Usually, CC imaging and MLO imaging are performed for diagnosis, and thus the diagnostic images acquired by the diagnostic image acquisition unit 51 are CC images and MLO images in which a calcification as the biopsy target is marked. The marking for a calcification means that information specifying the position of a calcification as the biopsy target is attached to a partial or entire diagnostic image. For example, attaching a marker, a label, or the like to a specific calcification in the diagnostic image to specify the position of the calcification and/or recording information such as coordinates indicating the position or the range of a specific calcification in association with the diagnostic image corresponds to the marking for a calcification. In the present embodiment, for the calcification as the biopsy target, a doctor attaches a specific marker to the diagnostic image, and the coordinates of the position of the marker are recorded in the header or the like of the diagnostic image.

Figure 3:
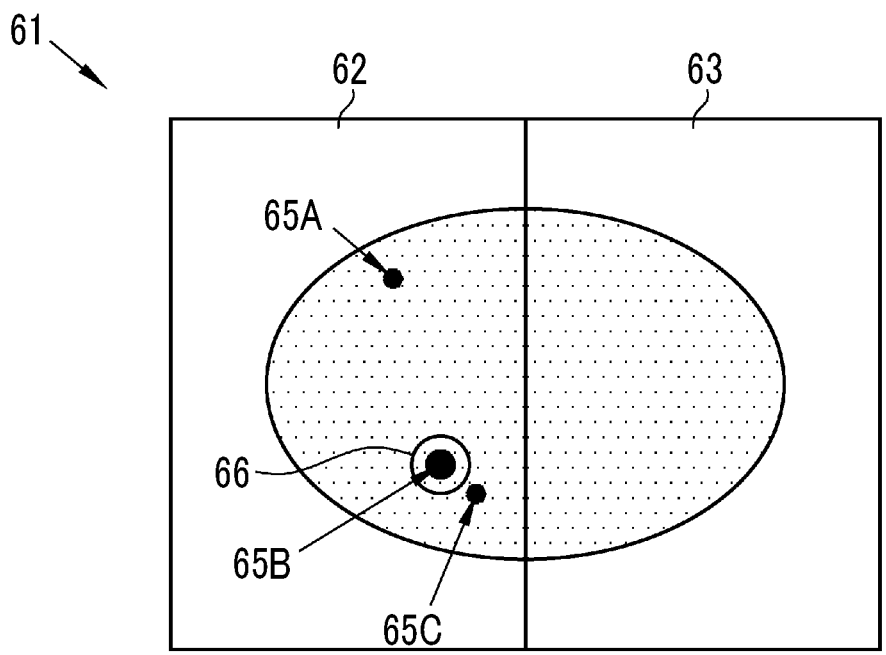
FIG. 3 is a CC image to be used for diagnosis.

As shown in FIG. 3, a CC image 61 as one of the diagnostic images is composed of a left mamma image 62 obtained by imaging the left mamma of the test subject from the CC direction, and a right mamma image 63 obtained by imaging the right mamma of the test subject from the CC direction. In the present embodiment, there are a plurality of calcifications 65A to 65C in the left mamma image 62. In addition, it is assumed that the doctor diagnoses that a biopsy is necessary for the calcification 65B among the calcifications 65A to 65C and marks the calcification 65B by attaching a marker 66, for example.

Figure 4:
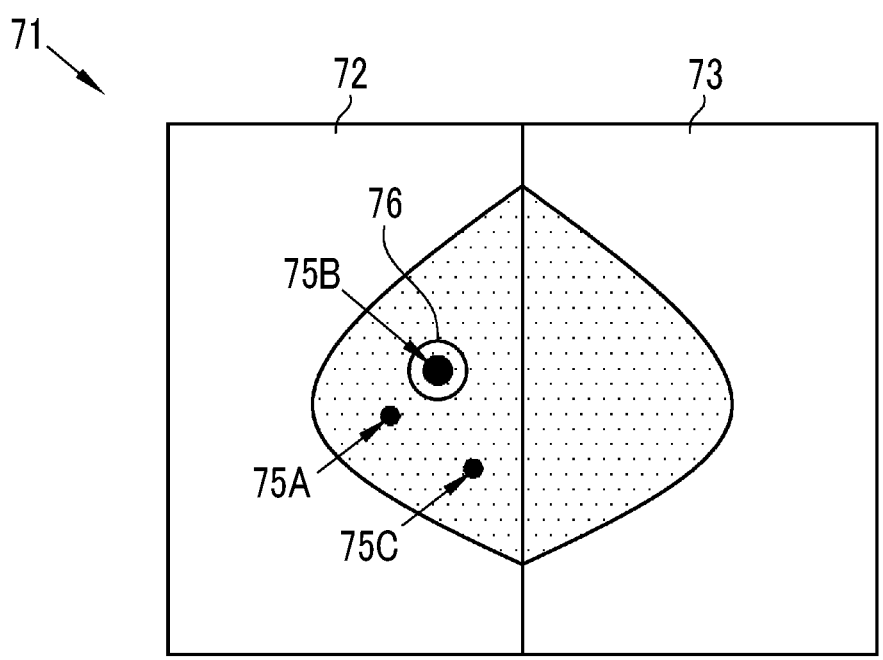
FIG. 4 is an MLO image to be used for diagnosis.

In addition, as shown in FIG. 4, an MLO image 71 as one of the diagnostic images is composed of a left mamma image 72 obtained by imaging the left mamma of the test subject from an inclination direction inclined by a predetermined angle (hereinafter, referred to as an MLO direction), and a right mamma image 73 obtained by imaging the right mamma of the test subject from the MLO direction. In the present embodiment, in the MLO image 71, there are a plurality of calcifications 75A to 75C in the left mamma image 72. Then, among the plurality of calcifications 75A to 75C in the MLO image 71, the calcification 75A corresponds to the calcification 65A in the CC image 61, the calcification 75B corresponds to the calcification 65B in the CC image 61, and the calcification 75C corresponds to the calcification 65C in the CC image 61. In addition, in the diagnosis, the doctor marks the calcification 75B by attaching a marker 76 to the calcification 75B of the MLO image 71.

Figure 5:
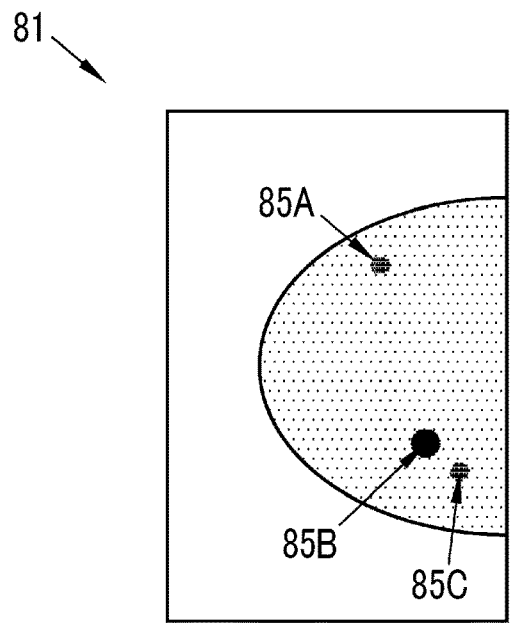
FIG. 5 is an example of a scout image which is one of biopsy images.

The scout image acquisition unit 52 acquires a scout image obtained by imaging the mamma undergoing the biological tissue examination from a specific direction. More specifically, in case of performing a biopsy, the scout image acquisition unit 52 controls the X-ray generation part 32 and the X-ray imaging part included in the imaging stand 33 to image the mamma of the test subject undergoing the biopsy, and thereby acquires a scout image 81 (refer to FIG. 5) as one of the biopsy images. The scout image 81 is a mammography image captured in order to search for a calcification as a biopsy target in case of performing a biopsy. In the present embodiment, as shown in FIG. 5, the scout image 81 is an image obtained by imaging the left mamma of the test subject from the CC direction, and a plurality of calcifications 85A to 85C are shown. These calcifications are candidates for the biological tissue examination. In general, the grid is not used in the capturing of a so-called scout image, and thus the scout image 81 acquired in the present embodiment is captured without using the grid. Note that, the mammography apparatus 10 can use a grid for capturing a scout image as necessary.

In case of performing a biopsy, the stereo image acquisition unit 53 acquires a stereo image obtained by imaging the mamma undergoing the biopsy, from an inclination direction which is inclined with respect to the specific direction from which the scout image 81 is captured. More specifically, the stereo image acquisition unit 53 controls the X-ray generation part 32 and the X-ray imaging part included in the imaging stand 33 to image the mamma from one or a plurality of inclination directions, and thereby acquires one or a plurality of stereo images. Since the stereo image is captured in case of performing a biopsy, the stereo image is the biopsy image. The stereo image is used in combination with the scout image in order to specify a three-dimensional position of the calcification (three-dimensional position within the mamma) as the biopsy target. In the present embodiment, the stereo image acquisition unit 53 images the mamma of the test subject from two inclination directions. Therefore, the stereo image acquisition unit 53 acquires a stereo image 101 and a stereo image 102 (refer to FIG. 6). The calcifications shown in the stereo image 101 and/or the stereo image 102 are candidates for the biological tissue examination.

The tomosynthesis image acquisition unit 54 acquires a series of tomosynthesis images of a mamma undergoing the biopsy. More specifically, in case of performing a biopsy, the tomosynthesis image acquisition unit 54 images the mamma of the test subject undergoing the biopsy a plurality of times while moving the X-ray generation part 32. Then, for the mamma of the test subject undergoing the biopsy, a series of tomosynthesis images consisting of one or a plurality of tomographic images is acquired using the obtained images. The acquisition of the tomosynthesis images by the tomosynthesis image acquisition unit 54 is performed as necessary. The calcification shown in the tomosynthesis image is a candidate for the biological tissue examination.

The tissue similarity degree calculation unit 55 recognizes a calcification in the scout image 81 and calculates a tissue similarity degree. The tissue similarity degree is a similarity degree between the calcification (candidate for the biological tissue examination) in the scout image 81 and the marked calcification 65B (target of the biological tissue examination) in the diagnostic image. In the present embodiment, the tissue similarity degree calculation unit 55 recognizes each of the three calcifications 85A to 85C in the scout image 81. Then, the tissue similarity degree calculation unit 55 calculates a tissue similarity degree between each of the calcifications 85A to 85C in the scout image 81 and the marked calcification 65B in the CC image 61 as one of the diagnostic images. That is, the tissue similarity degree calculation unit 55 calculates a tissue similarity degree between the calcification 85A and the calcification 65B, a tissue similarity degree between the calcification 85B and the calcification 65B, and a tissue similarity degree between the calcification 85C and the calcification 65B. As the value of the tissue similarity degree becomes larger, the similarity with the marked calcification 65B is high and the possibility that the calcification is the same as the marked calcification 65B is high.

The display unit 56 is configured of a display such as a liquid display device or the like and a control circuit thereof (display control unit), for example. The display unit 56 highlights at least "a candidate for the biological tissue examination in the scout image 81 which matches the marked target of the biological tissue examination in the diagnostic image". The "highlighting" for the candidate for the biological tissue examination refers to a display aspect in which the position, size, range, shape, or the like of one or a plurality of candidates for the biological tissue examination can be distinguished from other tissues or the like, and includes a display aspect in which the candidate for the biological tissue examination can be distinguished from other tissues by directly changing the display aspect of the candidate for the biological tissue examination, and a display aspect in which the candidate for the biological tissue examination can be indirectly distinguished from other tissues by changing the display aspect of other tissues or the like. For example, the display unit 56 can highlight the candidate for the biological tissue examination by using a method of surrounding the candidate for the biological tissue examination with a circle, an ellipse, a quadrangle, or the like, attaching a marker, a sign, or a symbol such as "O", "◊", or an arrow to the candidate for the biological tissue examination, displaying the candidate in association with a numerical value, a character, or the like, or changing a color, a density, or brightness of the candidate for the biological tissue examination or the other tissues.

The display unit 56 includes a determination unit 59. In the present embodiment, the determination unit 59 is one of the functions of the display control circuit configuring the display unit 56. However, the determination unit 59 can be provided separately from the display unit 56 and the display control circuit configuring the display unit 56. That is, the determination unit 59 may not be provided to be included in the display unit 56. The determination unit 59 determines whether the marked calcification 65B (target of the biological tissue examination) in the diagnostic image matches the calcifications 85A to 85C (candidates for the biological tissue examination) in the scout image 81. The display unit 56 decides the candidate for the biological tissue examination to be highlighted among the calcifications 85A to 85C in the scout image 81 by using the determination result of the determination unit 59. That is, the display unit 56 highlights the candidate for the biological tissue examination of which the tissue similarity degree is equal to or greater than a threshold (first threshold).

The determination unit 59 uses the tissue similarity degrees for the determination. Specifically, the determination unit 59 compares a predetermined threshold (first threshold) with the tissue similarity degree, and determines that the calcification (candidate for the biological tissue examination) having a tissue similarity degree equal to or greater than the threshold "matches" the marked calcification 65B (target of the biological tissue examination) in the diagnostic image. Conversely, the determination unit 59 determines that the calcification (candidate for the biological tissue examination) having a value of the tissue similarity degree less than the threshold "does not match" the marked calcification (target of the biological tissue examination) in the diagnostic image. That is, in the comparison between the marked target of the biological tissue examination in the diagnostic image and the candidate for the biological tissue examination in the biopsy image, the term "matching" refers to having a similarity equal to or greater than a certain level. Particularly, in the comparison between the marked calcification 65B (target of the biological tissue examination) in the diagnostic image and the calcifications 85A to 85C (candidate for the biological tissue examination) in the scout image 81, the term "matching" refers to having a tissue similarity degree equal to or greater than the predetermined threshold (first threshold).

The setting of the threshold that the determination unit 59 uses for determination can be arbitrarily changed according to the specific properties of the target of the biological tissue examination, for example. In addition, even in a case where there is one marked calcification 65B in the diagnostic image, the display unit 56 may highlight a plurality of calcifications, and in the plurality of calcifications, the calcification 85B (candidate for the biological tissue examination) actually matching the marked calcification 65B in the diagnostic image is included. The expression "actually matching" refers to actually the same or corresponding tissue or structure, or the like.

In the present embodiment, the tissue similarity degree is a nonnegative real number, and the threshold that the determination unit 59 uses for determination is, for example, "20". Therefore, in the determination of the determination unit 59 for determining at least the necessity of the highlighting, the calcification of which the tissue similarity degree is equal to or greater than "20" is treated to match the marked calcification 65B in the diagnostic image, and becomes the target to be highlighted by the display unit 56. As a result, the display unit 56 highlights the candidate (calcification 85B) of the biological tissue examination in the scout image 81 which is one of the candidates for the biological tissue examination recognized by the tissue similarity degree calculation unit 55 and matches the marked target (calcification 65B) of the biological tissue examination in the diagnostic image. In the present embodiment, the display unit 56 highlights the candidates for the biological tissue examination in the scout image 81 by attaching arrows to the candidates (calcifications 85A to 85C) of the biological tissue examination to indicate the positions thereof and displaying the value 110 of the tissue similarity degree.

Figure 6:
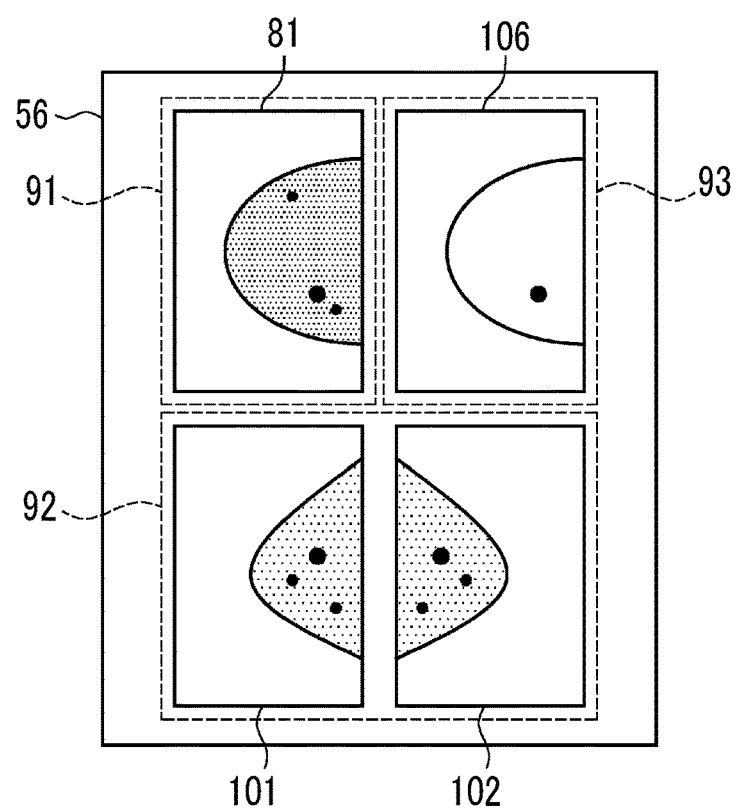
FIG. 6 is an explanatory diagram showing a display example of biopsy images on a display unit.

More specifically, the display unit 56 displays the position of the calcification (candidate for the biological tissue examination) in the scout image 81 which matches the marked calcification (target of the biological tissue examination) in the diagnostic image, by using the tissue similarity degree. Further, the display unit 56 displays the tissue similarity degree and the position of the calcification in the scout image 81 in an association manner. For example, as shown in FIG. 6, the display unit 56 has a scout image display area 91 where the scout image 81 is displayed, a stereo image display area 92 where the stereo image is displayed, and a tomosynthesis image display area 93 where the tomosynthesis image is displayed. The display unit 56 displays the tissue similarity degrees at the positions of the calcifications 85A to 85C in an association manner, for example, in the scout image display area 91. "Displaying" the tissue similarity degree includes an aspect in which the value 110 or the magnitude of the tissue similarity degree can be recognized in addition to directly displaying the value 110 of the tissue similarity degree (refer to FIG. 8). For example, a color according to the value 110 of the tissue similarity degree is attached to the calcifications 85A to 85C, or a marker having a color, a shape, or a size according to the value 110 of the tissue similarity degree is attached to the calcifications 85A to 85C. That is, displaying the tissue similarity degree is one aspect of highlighting the candidates for the biological tissue examination indicated by the "probability" that the candidate for the biopsy target is the target.

In the stereo image display area 92, for example, the stereo image 101 obtained by imaging the mamma of the test subject undergoing the biopsy from a first inclination direction, and the stereo image 102 obtained by imaging the mamma of the test subject undergoing the biopsy from an inclination direction different from the first inclination direction are displayed. In addition, in the tomosynthesis image display area 93, in a case where a series of tomosynthesis images is acquired for the mamma of the test subject undergoing the biopsy, one or a plurality of tomosynthesis images are selected and displayed. In FIG. 6, in the tomosynthesis image display area 93, selected one tomosynthesis image 106 is displayed. The tomosynthesis image 106 displayed in the tomosynthesis image display area 93 can be switched to another tomosynthesis image (another tomographic image among the series of tomosynthesis images).

The warning notification unit 57 notifies of a warning at least in a case where there is no calcification (candidate for the biological tissue examination) to be highlighted by the display unit 56. The case where there is no calcification to be highlighted by the display unit 56 is, for example, a case in which the tissue similarity degree calculation unit 55 is not able to recognize any one of the calcifications 85A to 85C in the scout image 81 and thus is not able to calculate the tissue similarity degree, a case in which there is no calcification having the tissue similarity degree equal to or greater than the predetermined threshold, and the like. The warning notification unit 57 notifies of a warning to prompt the recapturing of the scout image 81, for example. That there is no calcification of which the position is displayed on the display unit 56 can be caused by the fact that the scout image 81 is not appropriately captured. In a case where the biopsy is performed without correcting such a situation, the calcification as the biopsy target cannot be specified, and as a result, an accurate biopsy cannot be performed, which becomes a burden on the test subject. The warning notification unit 57 notifies of the warning using a message by a sound or display on the display unit 56, turning on or off of an indicator (including an indicator displayed on the display unit 56), or generating other sounds, light, or the like.

Hereinafter, an operation aspect of the mammography apparatus 10 configured as described above, in particular, an operation aspect of the mammography apparatus 10 in case of performing the biopsy is described. First, as a premise, a doctor or a radiation technician acquires the CC image 61 and the MLO image 71 which are the diagnostic images, for the mamma of the test subject using the mammography apparatus 10. Then, the doctor makes a diagnosis using the CC image 61 and the MLO image 71. In a case where the calcification that may be associated with the breast cancer is found in the CC image 61 and the MLO image 71, the doctor decides to perform a biopsy for the test subject. In this case, the doctor marks one or a plurality of calcifications as the biopsy target in the CC image 61 and/or the MLO image 71, and preserves the images in the PACS (more specifically, a digital imaging and communications in medicine (DICOM) server configuring the PACS), for example.

Figure 7:
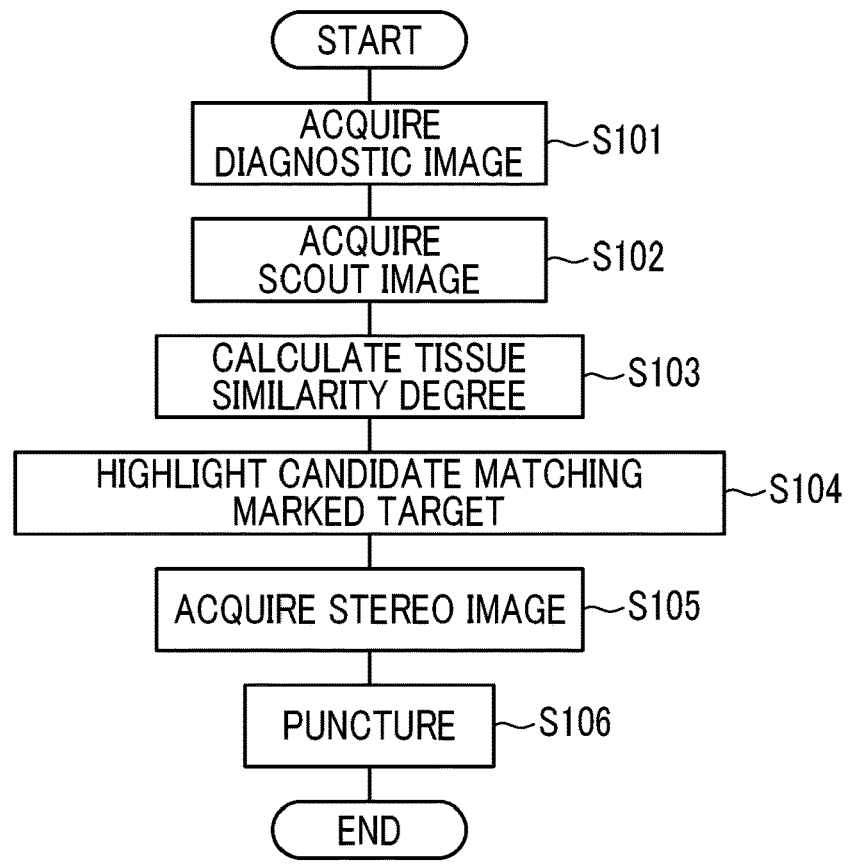
FIG. 7 is a flowchart showing an operation of a mammography apparatus in case of performing a biopsy.

Thereafter, in case of performing the biopsy, as shown in FIG. 7, the mammography apparatus 10 acquires the CC image 61 and/or the MLO image 71 as the diagnostic image by the diagnostic image acquisition unit 51 (step S101). For example, in a case where test subject information of the test subject undergoing the biopsy is set and registered in the mammography apparatus 10 or the like, the mammography apparatus 10 automatically performs this diagnostic image acquisition step before the biopsy. Of course, the diagnostic image acquisition step can be performed by an explicit operation input by the doctor or the like.

Meanwhile, the doctor or the radiation technician sets the mamma of the test subject undergoing the biopsy on the imaging stand 33, and inputs an instruction for execution of the scout imaging to the mammography apparatus 10. In this manner, the scout image acquisition unit 52 acquires the scout image 81 (step S102). In a case where the scout image acquisition unit 52 acquires the scout image 81, the tissue similarity degree calculation unit 55 recognizes the calcifications 85A to 85C in the scout image 81 and calculates the tissue similarity degree which is a similarity degree with the marked calcification 65B in the diagnostic image. In this manner, the tissue similarity degree calculation unit 55 calculates the tissue similarity degree for each of the calcifications 85A to 85C in the scout image 81 (step S103).

Figure 8:
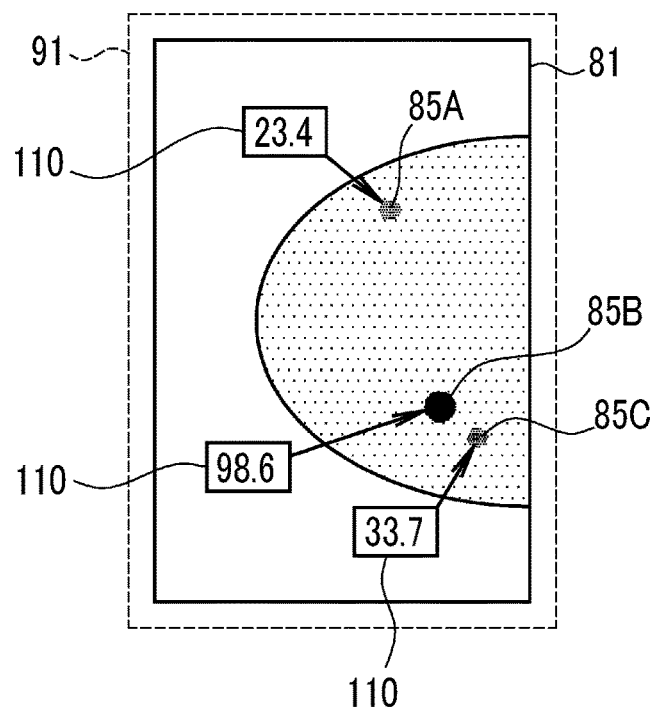
FIG. 8 is a display example of a tissue similarity degree.

In a case where the tissue similarity degree calculation unit 55 calculates the tissue similarity degree, the display unit 56 determines whether each of the calcifications 85A to 85C matches the marked calcification 65B in the diagnostic image using the tissue similarity degree by the determination unit 59. Then, the display unit 56 highlights the calcification which matches the marked calcification 65B in the diagnostic image, based on the determination result of the determination unit 59 (step S104). In the present embodiment, as a result of the determination of the determination unit 59, each of the calcifications 85A to 85C in the scout image 81 matches the marked calcification 65B in the diagnostic image. Therefore, the display unit 56 displays the positions of the calcifications 85A to 85C in the scout image 81, that is, the positions of candidates for the biological tissue examination. For example, as shown in FIG. 8, the display unit 56 indicates the position of each of the calcifications 85A to 85C using a leader line with an arrow from each of the calcifications 85A to 85C in the scout image 81, and indicates the specific value 110 of the tissue similarity degree of each of the calcifications 85A to 85C. In this manner, the display unit 56 displays the positions of the candidates for the biological tissue examination in the scout image 81 to overlap the scout image 81. In FIG. 8, the value 110 of the tissue similarity degree of the calcification 85A is "23.4" (%). Similarly, the value 110 of the tissue similarity degree of the calcification 85B is "98.6" (%), and the value 110 of the tissue similarity degree of the calcification 85C is "33.7" (%). Accordingly, the calcification 85B in the scout image 81 is the calcification which actually matches the calcification 65B (target of the biological tissue examination) in the CC image 61 marked during the diagnosis.

Thereafter, the doctor checks the display of the scout image 81 or the like on the display unit 56, and then inputs an instruction for acquiring a stereo image to the mammography apparatus 10. In this manner, the stereo image acquisition unit 53 acquires the stereo images 101 and 102 (step S105), and the stereo images 101 and 102 are displayed in the stereo image display area 92.

The doctor punctures the mamma of the test subject using a biopsy needle or the Mammotome while referring to the display of the images (step S106), and performs the biopsy. More specifically, the doctor specifies the calcification 85B as the biopsy target by referring to the display of the position and/or the tissue similarity degree of the calcification in the scout image 81. Further, the doctor performs the biopsy while checking the three-dimensional position of the calcification 85B as the biopsy target by referring to the stereo images 101 and 102.

As described above, in the mammography apparatus 10, the display unit 56 highlights at least a candidate for the biological tissue examination in the scout image 81 which matches the marked target of the biological tissue examination in the diagnostic image. Therefore, the doctor can easily and accurately capture the biopsy target specified in the diagnosis by the display of the scout image 81 and the highlighted candidates for the biological tissue examination. In the mammography apparatus in the related art in which such display is not performed, it has to specify the calcification as the biopsy target again using the scout image 81, and thus a calcification different from the calcification at the time of the diagnosis may incorrectly be collected in some cases. As compared with such a case, the mammography apparatus 10 can avoid an unnecessary or incorrect biopsy. As a result, the pain of the test subject is less as compared with the mammography apparatus in the related art. Further, since a situation in which the biopsy has to be performed again hardly occurs, at this point, the burden on the test subject can be reduced and the workflow of the biopsy can be improved.

The mammography apparatus 10 determines whether the marked calcification 65B in the diagnostic image matches the calcifications 85A to 85C in the scout image 81 using the tissue similarity degree indicating the similarity degree as the tissue structure, and determines whether to highlight the calcifications 85A to 85C in the scout image 81 according to the determination result. That is, the candidates for the biological tissue examination to be highlighted on the display unit 56 are only calcifications having a high similarity degree as the tissue structure with the marked calcification 65B in the diagnostic image. For example, in a case where all of the calcifications which can be recognized are highlighted without being subjected to the determination, if the number of calcifications is large, the display by the highlighting becomes complicated, which disturbs the specifying as the biopsy target, in some cases. In contrast, in the mammography apparatus 10, since the highlighting on the display unit 56 selectively displays only the actual biopsy target or the candidate having a high possibility to be the biopsy target, and the display aspect is simple, it is easy to capture the biopsy target by the scout image 81 and the highlighting on the scout image 81.

The mammography apparatus 10 can assist in capturing the biopsy target directly and accurately by displaying the tissue similarity degree. In a case where information is insufficient to identify the calcification as the target specified during the diagnosis simply by the fact that the position of the candidate (calcifications 85A to 85C in the embodiment) of the target in the biopsy image is similar to the position of the target specified during the diagnosis (in a case where the calcifications are dense or the like), it is possible to reduce the possibility of incorrectly recognizing an actual target with the near target candidates.

In the first embodiment, the tissue similarity degree is displayed in combination with the position of the candidate (calcification 85B and the like) of the biological tissue examination in the scout image 81, which matches the marked target (calcification 65B) of the biological tissue examination in the diagnostic image, but the display of the tissue similarity degree can be omitted. This is because the doctor or the like can distinguish the target of the biological tissue examination specified in the diagnostic image in a case where the position of one or a plurality of candidates for the biological tissue examination is displayed based on the tissue similarity degree, unless the calcifications are dense or the like. For example, there is a display aspect in which the arrows in FIG. 8 are left and the display of the value 110 of the tissue similarity degree (numerical values and parts surrounding the numerical values) is omitted.

Figure 9:
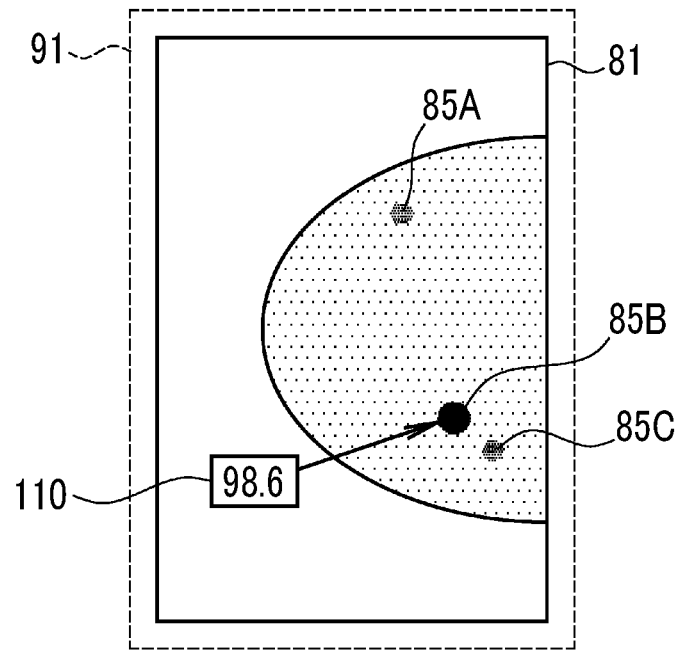
FIG. 9 is another display example of a tissue similarity degree.

In the first embodiment, the display unit 56 highlights all of the calcifications 85A to 85C recognized by the tissue similarity degree calculation unit 55 as a result of the determination, but the display unit 56 can selectively display the tissue similarity degree for some of the calcifications 85A to 85C recognized by the tissue similarity degree calculation unit 55 by adjusting the value of the threshold that the determination unit 59 uses for determination. In the first embodiment, the threshold that the determination unit 59 uses for determination is "20", but in a case where the setting of the value is changed to, for example, "70", the display unit 56 can selectively highlight only the calcification 85B which actually matches the marked calcification 65B in the diagnostic image (or only the calcification having high similarity with the calcification 65B, in particular) as shown in FIG. 9. That is, the display unit 56 can highlight only the actual biopsy target depending on the adjustment.

Second Embodiment

Figure 10:
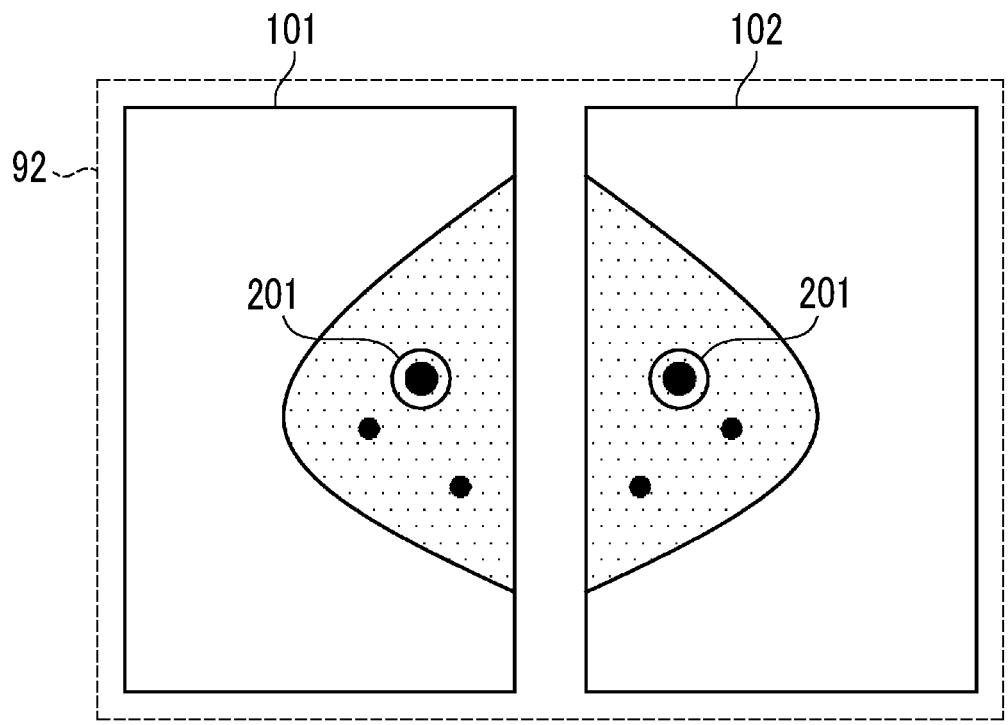
FIG. 10 is a display example showing a position of a target in a stereo image which is one of biopsy images.

In the first embodiment, specifying the calcification, which matches the calcification 65B marked during the diagnosis, in the scout image 81 is made easy by highlighting the candidates for the biological tissue examination in the scout image 81, but it is preferable to highlight the calcification which matches the calcification 65B marked during the diagnosis, in the stereo images 101 and 102 in addition to the highlighting of the candidates in the scout image 81 or instead of the highlighting in the scout image 81. For example, as shown in FIG. 10, a marker 201 is attached to the calcification which matches "the marked calcification 65B (or the calcification in the scout image 81 which matches the marked calcification 65B)" among the calcifications shown in the stereo image 101 and/or the stereo image 102, and is highlighted. This is because it becomes easy to grasp the three-dimensional position of the calcification 85B as the biopsy target.

Figure 11:
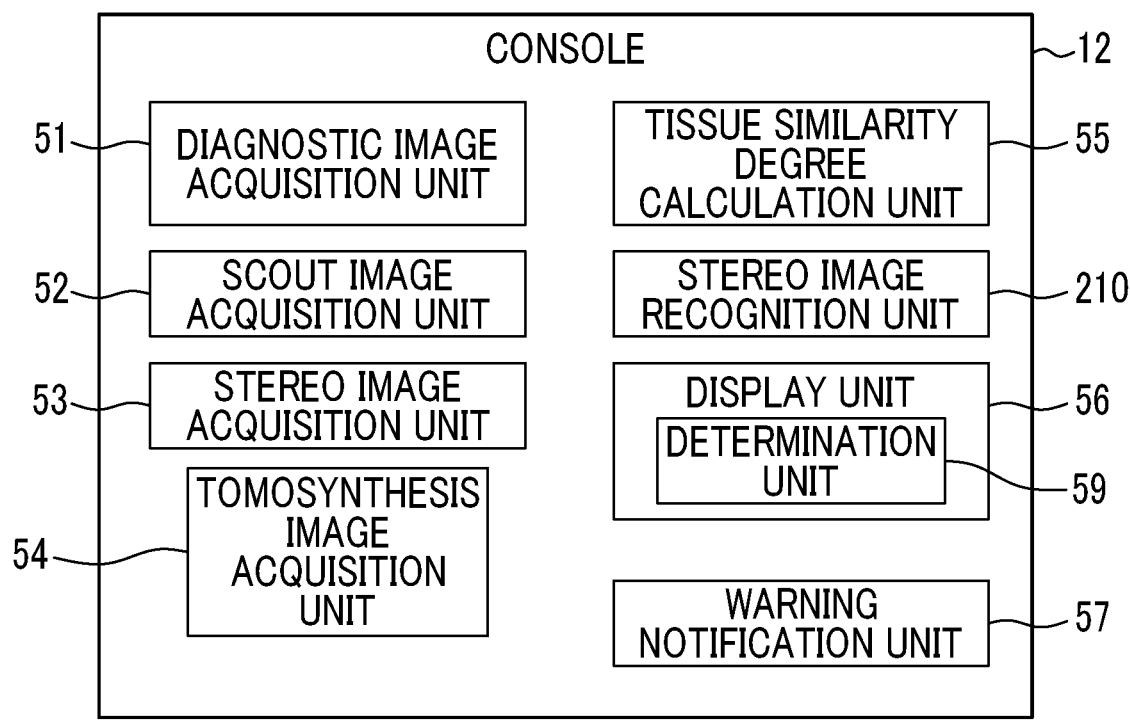
FIG. 11 is a block diagram showing a configuration of a console according to a second embodiment.

In this case, as shown in FIG. 11, the console 12 is provided with a stereo image recognition unit 210. The stereo image recognition unit 210 recognizes the calcifications in the stereo images 101 and 102, and associates the calcifications in the stereo images 101 and 102 with "the marked calcification 65B in the diagnostic image (or the calcification in the scout image 81 which matches the marked calcification 65B in the diagnostic image)". Using a result of this association, the display unit 56 highlights the calcification which matches the marked calcification 65B in the diagnostic image, among calcifications in the stereo images 101 and 102. In this manner, the biopsy target can be accurately displayed also in the stereo images 101 and 102. As a result, it is possible to assist in grasping the three-dimensional position of the biopsy target.

The association process performed by the stereo image recognition unit 210 can be performed by calculating a second tissue similarity degree which is a similarity degree between the calcification in the stereo images 101 and 102 and the marked calcification 65B in the diagnostic image or the calcification 85B in the scout image 81 which matches the marked calcification 65B in the diagnostic image, for example. In this case, the display unit 56 highlights at least the calcification having the highest second tissue similarity degree, among the calcifications in the stereo images 101 and 102. In this manner, the biopsy target can be accurately displayed also in the stereo images 101 and 102. Of course, the display unit 56 may set a threshold for determining whether to perform highlighting, for the second tissue similarity degree.

In the second embodiment, the candidates for the biological tissue examination in the stereo images 101 and 102 are highlighted, but in addition to the highlighting of the candidates for the biological tissue examination, the value of the second tissue similarity degree can be displayed in the stereo images 101 and 102. In a case where the value of the second tissue similarity degree is displayed, it is possible to assist in capturing the biopsy target directly and accurately. This is the same reason as the case in which the tissue similarity degree is displayed in the scout image 81.

In the first and second embodiments, in a case where there is no calcification, which matches the marked calcification 65B in the diagnostic image, in the scout image 81, it is preferable that the stereo image acquisition unit 53 prohibits the capturing of the stereo images 101 and 102. This is because, even if the stereo images 101 and 102 are captured without correcting such a situation, a probability of obtaining stereo images 101 and 102 including the calcification as the biopsy target is low, and as a result, useless exposure is increased, which becomes a burden on the test subject.

Third Embodiment

In the first and second embodiments, in case of performing the tomosynthesis imaging, since the tomosynthesis image display area 93 is limited, one or a plurality of tomosynthesis images (in the embodiments, one tomosynthesis image 106) are selectively displayed from among a series of tomosynthesis images consisting of a plurality of tomosynthesis images. However, it is not easy to select a tomosynthesis image in which the biopsy target is appropriately shown from among a series of tomosynthesis images. Therefore, in case of performing the tomosynthesis imaging, it is preferable that the mammography apparatus 10 assists in selecting the tomosynthesis image 106 to be displayed on the display unit 56.

Figure 12:
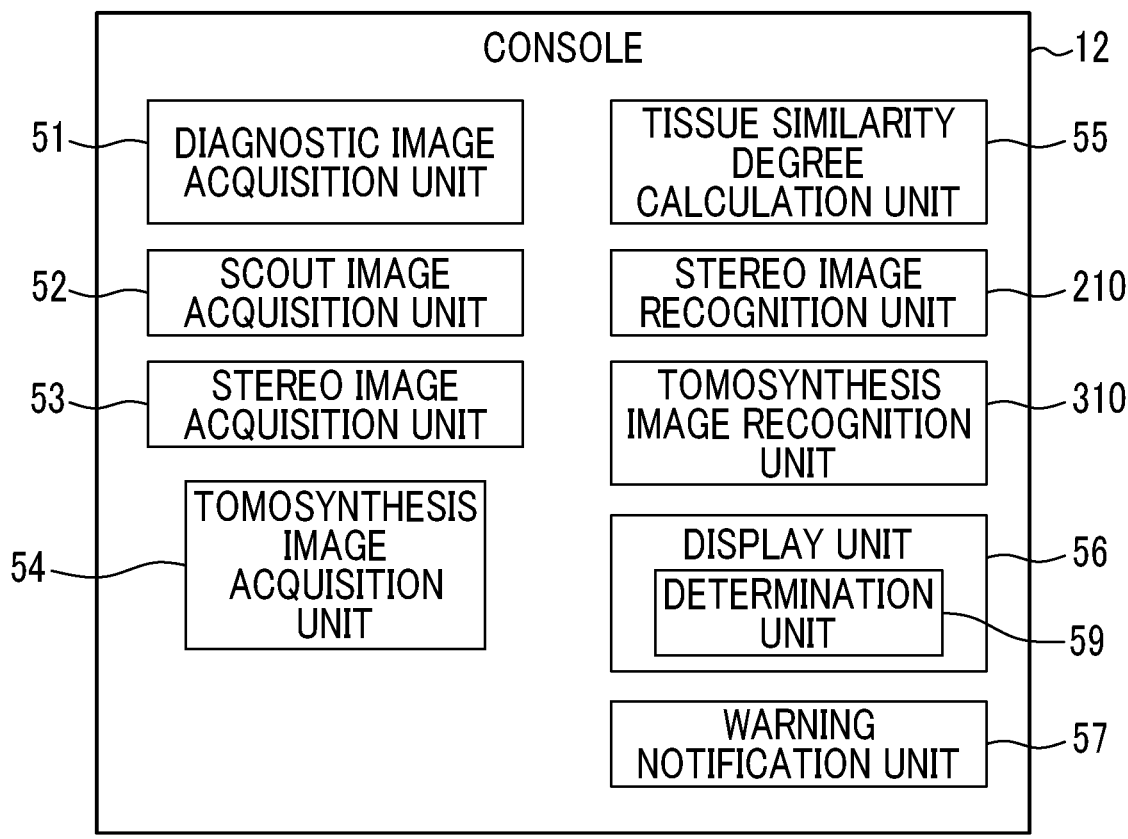
FIG. 12 is a block diagram showing a configuration of a console according to a third embodiment.

In this case, as shown in FIG. 12, the console 12 is provided with a tomosynthesis image recognition unit 310. The tomosynthesis image recognition unit 310 recognizes the calcifications in a series of tomosynthesis images, and associates the calcification in each tomosynthesis image with the marked calcification 65B in the diagnostic image or the calcification in the scout image 81 which matches the marked calcification 65B in the diagnostic image. Using a result of the recognition and the association (recognition result of the tomosynthesis image recognition unit 310), the display unit 56 selects and displays some tomosynthesis images from among a series of tomosynthesis images. That is, in the present embodiment, the display unit 56 selects and displays one or a plurality of tomosynthesis images 106 including the calcification matching the marked calcification 65B in the diagnostic image, from among calcifications in a series of tomosynthesis images. In this manner, it is possible to assist in capturing the biopsy target by displaying the tomosynthesis image 106, in which the biopsy target is appropriately shown, in the limited tomosynthesis image display area 93.

The association process performed by the tomosynthesis image recognition unit 310 can be performed by calculating a third tissue similarity degree which is a similarity degree between the calcification in the tomosynthesis image and the marked calcification 65B in the diagnostic image or the calcification in the scout image 81 which matches the marked calcification 65B in the diagnostic image, for example. In this case, the display unit 56 displays at least the tomosynthesis image 106 including the calcification having the highest third tissue similarity degree, among the calcifications in a series of tomosynthesis images. In this manner, it is possible to display an appropriate tomosynthesis image 106 including the biopsy target from among a series of tomosynthesis images. Of course, the display unit 56 may set a threshold for determining whether to perform highlighting, for the third tissue similarity degree.

In the third embodiment, the third tissue similarity degree is used only for the selection of the tomosynthesis image 106, but the candidates for the biological tissue examination may be highlighted at least in the tomosynthesis image 106 selected for display. For example, similar to the first embodiment or the second embodiment, it is possible to highlight some or all of the recognized calcifications in the tomosynthesis image 106 using the third tissue similarity degree. In addition to the highlighting indicating the position or the like of the candidate for the biological tissue examination, the value of the third tissue similarity degree can be displayed in the tomosynthesis image 106. In a case where the value of the third tissue similarity degree is displayed, it is possible to assist in capturing the biopsy target directly and accurately. This is because it is possible to easily check that the candidate for the biological tissue examination of which the position is indicated is similar to the biopsy target specified in the diagnostic image. In a case where the position of the candidate for the biological tissue examination is indicated by the highlighting in the tomosynthesis image 106, the highlighting for indicating the position of the candidate for the biological tissue examination in the scout image 81 and/or the stereo images 101 and 102 may be omitted. This is because the position of the calcification can be checked in the tomosynthesis image 106. Note that, it is preferable that the highlighting for indicating the position of the candidate for the biological tissue examination in the tomosynthesis image 106 is used in combination with the highlighting for indicating the position of the candidate for the biological tissue examination in the scout image 81 and/or the stereo images 101 and 102. This is for more accurately specifying the position of the candidate for the biological tissue examination.

In the first, second, and third embodiments, in a case where there is no calcification, which matches the marked calcification 65B in the diagnostic image, in the scout image 81, it is preferable that the tomosynthesis image acquisition unit 54 prohibits the imaging for obtaining the tomosynthesis image. This is because, even if the tomosynthesis imaging is performed without correcting such a situation, a probability of obtaining a tomosynthesis image including the calcification as the biopsy target is low, and as a result, useless exposure is increased, which becomes a burden on the test subject.

Fourth Embodiment

In the first, second, and third embodiments, whether the display unit 56 highlights the candidates for the biological tissue examination in the scout image 81 is determined using the determination result of the determination unit 59 based on the tissue similarity degree, but it is preferable that whether to highlight the candidates for the biological tissue examination in the scout image 81 is determined in consideration of the similarity between the diagnostic image (CC image 61 or MLO image 71) with the scout image 81 as the whole image. This is because, in a case where the image of the mamma of the subject shown in the diagnostic image is not similar to that shown in the scout image 81 as the whole image, even if the similarity in a limited region such as a calcification portion (vicinity of the candidates for the biological tissue examination) is high, the possibility that the calcification does not actually match the marked calcification (target of the biological tissue examination) in the diagnostic image is high.

Figure 13:
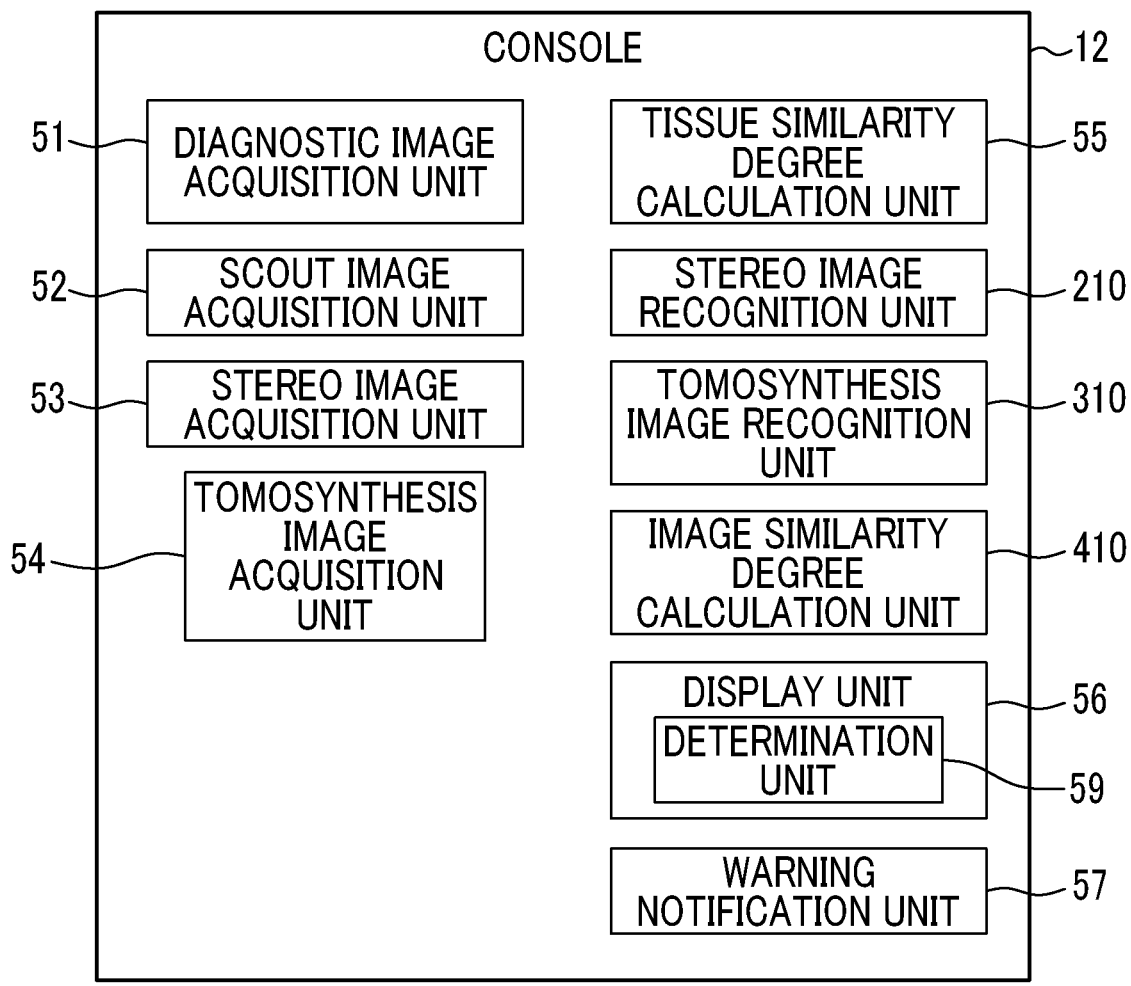
FIG. 13 is a block diagram showing a configuration of a console according to a fourth embodiment.

In a case where whether to highlight the candidates for the biological tissue examination is determined in consideration of the similarity between the diagnostic image and the scout image 81 as the whole image, as shown in FIG. 13, the console 12 is provided with an image similarity degree calculation unit 410. The image similarity degree calculation unit 410 calculates an image similarity degree as a similarity degree for a partial image or a whole image between the diagnostic image and the scout image 81. Then, whether the display unit 56 highlights the candidate for the biological tissue examination is determined using the image similarity degree. For example, the display unit 56 sets a predetermined threshold (hereinafter, referred to as a second threshold) for the image similarity degree. The display unit 56 highlights the candidate for the biological tissue examination in a case where the value 110 of the image similarity degree is equal to or greater than the second threshold. In doing so, in a case where there is a difference in the shape or the like of the image of the mamma such that the diagnostic image and the scout image 81 are not similar as a whole image (or the entire region of interest specified or the like), it is possible to prevent that the calcification which has high similarity of the shape or the like of the calcification (high tissue similarity degree) but actually is not a real target is displayed, and to improve the reliability for the display of the position of the candidate for the biological tissue examination.

The term "portion" of the diagnostic image and the scout image 81 in the fourth embodiment does not mean a very small region (for example, a region close to actually a "point") such as a calcification, and is a portion having a size (area) enough to discriminate a shape or the like of the tissue of the mamma of the test subject in addition to the calcification as the biopsy target or the candidate thereof, for example, a region of interest having a size enough to include the entire image of one or a plurality of calcifications.

Figure 14:
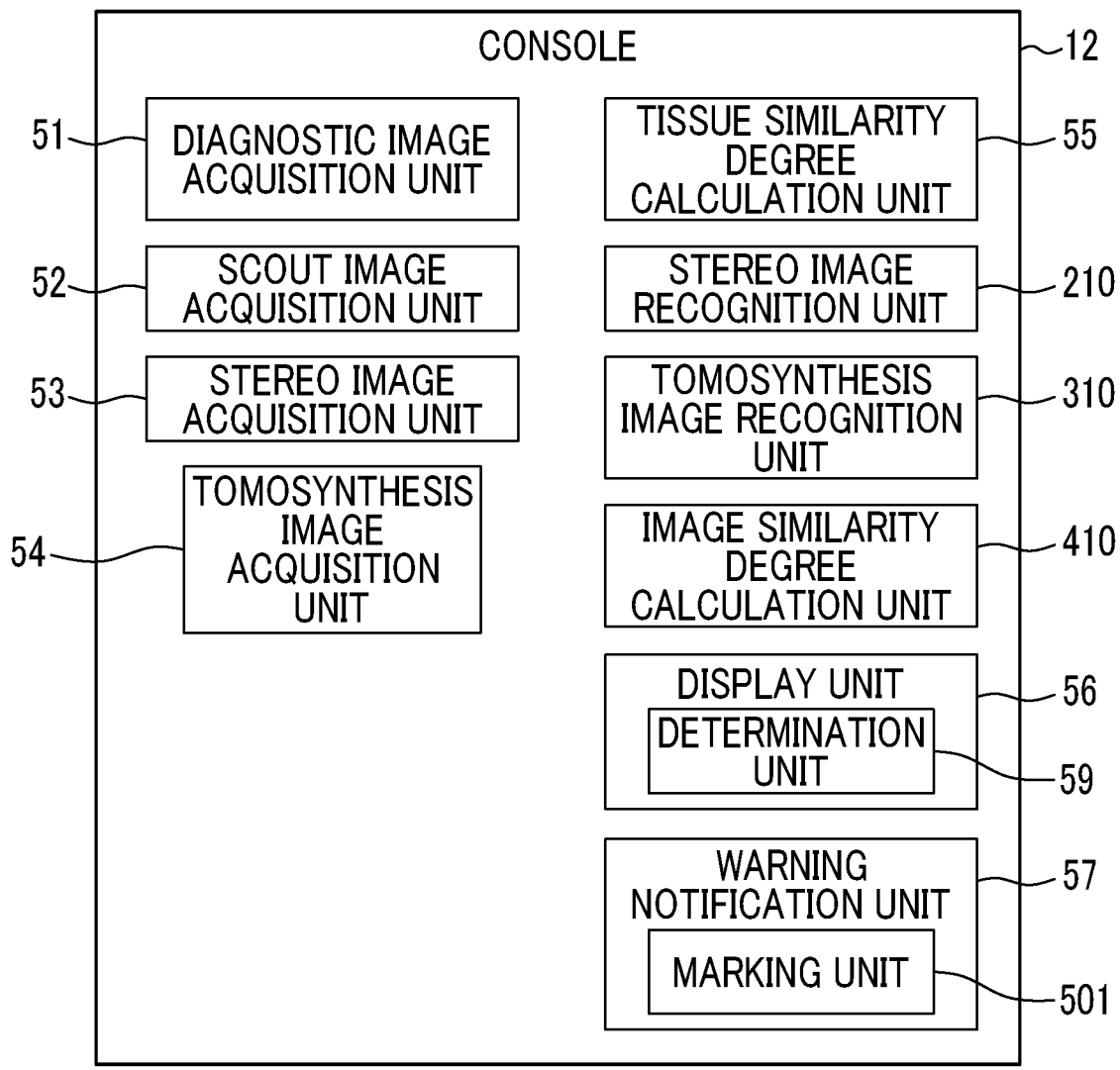
FIG. 14 is a block diagram showing a configuration of a console of a modification example.

In the above-described embodiments and the modification example, it is assumed that the biopsy target is marked in the diagnostic image. Accordingly, in a case where there is no marked calcification 65B in the diagnostic image, it is preferable that the warning notification unit 57 notifies of a warning to prompt the marking of a calcification. This is for effectively utilizing the assistance in capturing the target by the mammography apparatus 10. As shown in FIG. 14, for example, a marking unit 501 is provided to the warning notification unit 57, and the doctor or the like may mark the biopsy target in the diagnostic image on the spot using the marking unit 501. In a case where the marking unit 501 is a so-called computer-aided diagnosis (CAD) program and there is no marked calcification in the diagnostic image, the marking unit 501 provides a function of recognizing calcifications in the diagnostic image and marking some or all of the recognized calcifications.

In the above-described embodiments and the modification example, since the scout image 81 is a biopsy image, the scout image 81 is captured under an imaging condition different from that of the diagnostic image. For example, a grid is not used. However, the scout image acquisition unit 52 can acquire a scout image of which at least one or a plurality conditions among use or non-use of a grid, a tube voltage of the X-ray tube (in case of using other radiation, a radiation tube generating the radiation), and a dose of the X-rays (radiation) are the same as the diagnostic image. In this manner, in a case where the scout image acquisition unit 52 acquires a scout image 81 captured under the same imaging condition as that of the diagnostic image, the tissue similarity degree between the marked calcification 65B in the diagnostic image and the corresponding calcification 85B in the scout image 81 becomes high, and conversely, the tissue similarity degree between the marked calcification 65B with the other calcifications 85A and 85C in the scout image 81 becomes low. Accordingly, it is possible to highlight the calcification 85B as the biopsy target to be distinguished from the other calcifications 85A and 85C.

In particular, in a case where the scout image acquisition unit 52 acquires a scout image 81 in which the grid is used, it is preferable to acquire a scout image 81 in which a grid having the same grid ratio as the grid used for capturing the diagnostic image is used. This is for specifying the calcification 85B as the biopsy target with particularly high accuracy.

In addition, in a case where the scout image acquisition unit 52 can acquire a scout image 81 subjected to the image processing, it is preferable that the scout image acquisition unit 52 acquires a scout image 81 subjected to the same image processing as the diagnostic image. This is for distinguishing the calcification 85B, which is the biopsy target, more accurately from the other calcifications 85A and 85C.

In the above described modification example, parameters such as the imaging condition (tube voltage or the like) at the time of capturing the diagnostic image and the type, strength, or the like of the image processing performed at the time of acquiring the diagnostic image are attached to the diagnostic image or preserved in association with the diagnostic image, for example. Therefore, the scout image acquisition unit 52 can acquire information directly from the diagnostic image and indirectly via the diagnostic image acquisition unit 51.

In the embodiments and the modification example, the tissue similarity degree calculation unit 55 can recognize calcifications in the scout image 81 by so-called pattern matching and calculate the tissue similarity degree. Similarly, the stereo image recognition unit 210 and the tomosynthesis image recognition unit 310 can recognize the calcifications by the pattern matching.

Instead of the pattern matching, the tissue similarity degree calculation unit 55 can use a "learned model" (so-called artificial intelligence (AI) program) which outputs a probability that the calcification in the scout image 81 is the marked calcification 65B in the diagnostic image by inputting the diagnostic image in which the calcification 65B as the biopsy target is marked and the scout image 81 to specify the position of the calcification and output the "probability" that the learned model outputs as the tissue similarity degree. In addition, the tissue similarity degree calculation unit 55 can be configured by the AI program which causes an arithmetic operation device (combination of CPU, GPU, and/or a memory) of the mammography apparatus 10 or an arithmetic operation device cooperating with the mammography apparatus 10 to calculate the tissue similarity degree using the learned model which outputs the positions of the calcifications 85A to 85C in the scout image 81 and the tissue similarity degree as the similarity degree between the calcifications 85A to 85C in the scout image 81 and the marked calcification 65B in the diagnostic image by inputting the diagnostic image and the scout image 81 (biopsy image). Similarly, the pattern matching or the learned model can be used for the recognition processing or the like in the stereo image recognition unit 210, the tomosynthesis image recognition unit 310, and/or the image similarity degree calculation unit 410. It is possible to configure each of units by using the AI program in which learned models having the functions of the units are used.

In the above-described embodiments or the like, the mammography apparatus 10 is described as an example, but the present invention can be preferably used in a radiographic apparatus or an ultrasonic inspection apparatus that can perform the biological tissue examination. These apparatuses can be configured using the diagnostic image acquisition unit that acquires a diagnostic image in which a target of the biological tissue examination is marked, the image acquisition unit that acquires a biopsy image in which the subject undergoing the biological tissue examination is shown in a case where the biological tissue examination is performed, and the display unit that highlights the candidates for the biological tissue examination in the biopsy image matching at least the marked target of the biological tissue examination in the diagnostic image.

In the above-described embodiments, the hardware structures of the processing unit executing various processing such as the tissue similarity degree calculation unit 55, the determination unit 59, the stereo image recognition unit 210, the tomosynthesis image recognition unit 310, and the image similarity degree calculation unit 410 are various processors described below. The various processors include a central processing unit (CPU) and a graphical processing unit (GPU) as a general-purpose processor executing software (program) and functioning as various processing units, a programmable logic device (PLD) as a processor of which the circuit configuration can be changed after manufacturing such as a field programmable gate array (FPGA), a dedicated electrical circuit as a processor having a circuit configuration designed exclusively for executing various processing, and the like.

One processing unit may be configured by one of the various processors, or configured by the combination of the same or different kinds of two or more processors (for example, combination of a plurality of FPGAs, combination of the CPU and the FPGA, combination of the CPU and the GPU, or the like). Further, a plurality of processing units may be configured by one processor. As an example where a plurality of processing units are configured by one processor, first, there is an aspect where one processor is configured by a combination of one or more CPUs and software as typified by a computer, such as a client or a server, and this processor functions as a plurality of processing units. Second, there is an aspect where a processor fulfilling the functions of the entire system including a plurality of processing units by one integrated circuit (IC) chip as typified by a system on a chip (SoC) or the like is used. In this way, various processing units are configured using one or more of the above-described various processors as hardware structures.

Furthermore, the hardware structures of the various processors are more specifically electrical circuitry in a form in which circuit elements, such as semiconductor elements, are combined.

EXPLANATION OF REFERENCES

10: mammography apparatus
11: apparatus body
12: console
31: prop
32: X-ray generation part
33: imaging stand
34a: grip part
34b: grip part
36: pressing plate
37: lifting/lowering part
40: movable part
51: diagnostic image acquisition unit
52: scout image acquisition unit
53: stereo image acquisition unit
54: tomosynthesis image acquisition unit
55: tissue similarity degree calculation unit
56: display unit
57: warning notification unit
59: determination unit
61: CC image 62: left mamma image
63: right mamma image
65A to 65C: calcification
66: marker
71: MLO image
72: left mamma image
73: right mamma image
75A to 75C: calcification
76: marker
81: scout image
85A to 85C: calcification
91: scout image display area
92: stereo image display area
93: tomosynthesis image display area
101, 102: stereo image
106: tomosynthesis image
110: value of tissue similarity degree
201: marker
210: stereo image recognition unit
310: tomosynthesis image recognition unit
410: image similarity degree calculation unit
501: marking unit
S101 to S106: operation step

What is claimed is:

1. A mammography apparatus comprising:
a processor configured to:
    acquire a diagnostic image which is a mammography image of a patient, wherein the diagnostic image comprises an indicator marked by a medical staff to indicate a target to be undergoing a biopsy;
    in response to an instruction to perform the biopsy on the patient being received after the diagnostic image is acquired, image a mamma of the patient undergoing the biopsy from a specific direction to acquire a scout image;
    notify of a warning in a case where there is no indicated target in the diagnostic image;
    determine whether a candidate for the biopsy in the scout image matches the indicated target in the diagnostic image; and
    highlight on a display the candidate for the biopsy in the scout image determined to be matching the indicated target in the diagnostic image.

2. The mammography apparatus according to claim 1, the processor further configured to:
    recognize the candidate for the biopsy in the scout image and calculate a tissue similarity degree which is a similarity degree between the candidate in the scout image and the indicated target in the diagnostic image; and
    determine whether the candidate matches the indicated target using the calculated tissue similarity degree.

3. The mammography apparatus according to claim 2, wherein the processor displays on the display a value of the tissue similarity degree.

4. The mammography apparatus according to claim 2, wherein the processor highlights on the display the candidate of which the tissue similarity degree is equal to or greater than a first threshold.

5. The mammography apparatus according to claim 1, the processor further configured to:
    calculate an image similarity degree which is a similarity degree for a partial image or a whole image between the diagnostic image and the scout image, and
    determine whether to highlight on the display the candidate using the image similarity degree.

6. The mammography apparatus according to claim 5, wherein the processor highlights on the display the candidate in a case where the image similarity degree is equal to or greater than a second threshold.

7. The mammography apparatus according to claim 1, wherein the processor notifies of a warning at least in a case where there is no candidate for the biopsy in the scout image to be highlighted by the display.

8. The mammography apparatus according to claim 7, wherein the processor prompts recapturing of the scout image as the warning notification.

9. The mammography apparatus according to claim 1, wherein the processor displays on the display a position of the candidate in the scout image determined to be matching the indicated target in the diagnostic image, by highlighting.

10. The mammography apparatus according to claim 1, the processor further configured to:
    acquire a stereo image obtained by imaging the mama a undergoing the biopsy from an inclination direction which is inclined with respect to the specific direction from which the scout image is captured;
    recognize the candidate in the stereo image, and associates the candidate in the stereo image with the indicated target in the diagnostic image or the candidate in the scout image which matches the indicated target in the diagnostic image; and
    highlight on the display the candidate matching the indicated target in the diagnostic image among the candidates in the stereo image.

11. The mammography apparatus according to claim 10, wherein the processor calculates a second tissue similarity degree which is a similarity degree between the candidate in the stereo image and the indicated target in the diagnostic image or the candidate in the scout image which matches the indicated target in the diagnostic image, and
    highlights on the display at least the candidate having a highest second tissue similarity degree among the candidates in the stereo image.

12. The mammography apparatus according to claim 10, wherein the processor prohibits capturing of the stereo image in a case where there is no candidate in the scout image, which matches the indicated target in the diagnostic image.

13. The mammography apparatus according to claim 1, the processor further configured to:
    acquire a series of tomosynthesis images of the mamma undergoing the biopsy;
    recognize the target of the biopsy in the series of tomosynthesis images, and associates the candidate in each tomosynthesis image with the indicated target in the diagnostic image or the candidate in the scout image which matches the indicated target in the diagnostic image; and
    select and display on the display some of the tomosynthesis images from among the series of tomosynthesis images using a recognition result of the tomosynthesis image recognition.

14. The mammography apparatus according to claim 13, wherein the processor calculates a third tissue similarity degree which is a similarity degree between the candidate in the tomosynthesis image and the indicated target in the diagnostic image or the candidate in the scout image which matches the indicated target in the diagnostic image, and displays on the display the tomosynthesis image including at least a calcification having a highest third tissue similarity degree among calcifications in the series of tomosynthesis images.

15. The mammography apparatus according to claim 13, wherein the processor prohibits imaging for obtaining the tomosynthesis image in a case where there is no candidate in the scout image, which matches the indicated target in the diagnostic image.

16. The mammography apparatus according to claim 1, wherein the processor recognizes the candidates in the diagnostic image and indicates some or all of the recognized candidates in a case where there is no indicated target in the diagnostic image.

17. The mammography apparatus according to claim 1, wherein the processor acquires the scout image of which at least one or a plurality conditions among use or non-use of a grid, a tube voltage of a radiation tube, and a dose of radiation are the same as the diagnostic image.

18. The mammography apparatus according to claim 17, wherein the processor acquires the scout image in which a grid having the same grid ratio as a grid used for capturing the diagnostic image is used in a case where the scout image in which the grid is used is acquired.

19. The mammography apparatus according to claim 1, wherein the processor acquires the scout image subjected to the same image processing as the diagnostic image.

20. The mammography apparatus according to claim 2, wherein the processor recognizes the candidate in the scout image by pattern matching and calculates the tissue similarity degree.

21. The mammography apparatus according to claim 2, wherein the processor outputs a probability that the candidate in the scout image is the indicated target in the diagnostic image, as the tissue similarity degree by using a learned model that outputs the probability by inputting the diagnostic image in which the target is indicated and the scout image.

22. An image processing method comprising:
acquire a diagnostic image which is a mammography image of a patient in which a target to be undergoing a biopsy has been specified by a medical staff;
after the diagnostic image is acquired, image a mamma of the patient undergoing the biopsy from a specific direction to acquire a scout image;
recognize a candidate for the biopsy in the scout image and calculate a tissue similarity degree which is a similarity degree between the candidate in the scout image and the indicated target in the diagnostic image; and
highlight on a display the candidate for the biopsy in the scout image when the tissue similarity degree is greater than a predetermined threshold.

23. The image processing method according to claim 22, wherein the mammography image is captured while the mamma of the patient is being pressed, and
wherein the scout image is captured while the mamma of the patient is being pressed.

24. The image processing method according to claim 22 further comprising:
perform a biopsy on the highlighted candidate, wherein the biopsy is performed while the mamma of the patient is in a state of being pressed at a time of capturing the scout image.

* * * * *